(12) United States Patent
Lebrun et al.

(10) Patent No.: US 6,566,587 B1
(45) Date of Patent: May 20, 2003

(54) MUTATED 5-ENOLPYRUVYLSHIKIMATE-3-PHOSPHATE SYNTHASE, GENE CODING FOR SAID PROTEIN AND TRANSFORMED PLANTS CONTAINING SAID GENE

(75) Inventors: Michel Lebrun, Lyons (FR); Alain Sailland, Lyons (FR); Georges Freyssinet, St Cyr Au Mont d'Or (FR); Eric Degryse, Strasbourg (FR)

(73) Assignee: Bayer CropScience S.A., Lyons (FR)

( * ) Notice: Subject to any disclaimer, the term of this patent is extended or adjusted under 35 U.S.C. 154(b) by 0 days.

(21) Appl. No.: 08/945,144

(22) PCT Filed: Jul. 18, 1996

(86) PCT No.: PCT/FR96/01125

§ 371 (c)(1),
(2), (4) Date: Jan. 20, 1998

(87) PCT Pub. No.: WO97/04103

PCT Pub. Date: Feb. 6, 1997

(30) Foreign Application Priority Data

Jul. 19, 1995 (FR) .............................................. 95 08979

(51) Int. Cl.⁷ .......................... C12N 15/82; C12N 5/10; A01H 5/00; C07H 21/04
(52) U.S. Cl. .................... 800/300; 435/419; 435/320.1; 47/58.1; 536/23.6; 800/320.1; 800/278; 800/287
(58) Field of Search ............................... 536/23.2, 23.6; 47/58.1; 435/410, 413, 419, 430.1, 440; 800/300, 320.1

(56) References Cited

U.S. PATENT DOCUMENTS

| | | | |
|---|---|---|---|
| 4,535,060 A | 8/1985 | Comai | 435/252.33 |
| 4,769,061 A | 9/1988 | Comai | 504/206 |
| 4,940,835 A | 7/1990 | Shah et al. | 800/288 |
| 4,971,908 A | 11/1990 | Kishore et al. | 536/23.2 |
| 5,013,659 A | 5/1991 | Bedbrook et al. | 536/23.2 |
| 5,094,945 A | 3/1992 | Comai | 435/6 |
| 5,145,783 A | 9/1992 | Kishore et al. | 800/300 |
| 5,188,642 A | * 2/1993 | Shah et al. | 47/58 |
| 5,310,667 A | 5/1994 | Eichholtz et al. | 435/91.1 |
| 5,312,910 A | 5/1994 | Kishore et al. | 536/23.2 |
| 5,378,619 A | 1/1995 | Rogers | 800/294 |
| 5,424,412 A | 6/1995 | Brown et al. | 536/24.1 |
| 5,510,471 A | 4/1996 | Lebrun et al. | 536/23.4 |
| 5,554,798 A | 9/1996 | Lundquist et al. | 800/300.1 |
| 5,605,011 A | 2/1997 | Bedbrook et al. | 47/58.1 R |
| 5,627,061 A | 5/1997 | Barry et al. | 800/288 |
| 5,633,435 A | 5/1997 | Barry et al. | 800/288 |

FOREIGN PATENT DOCUMENTS

| | | |
|---|---|---|
| EP | 293358 | 11/1988 |
| EP | 0507698 | 7/1992 |
| WO | WO 91/04323 | 4/1991 |
| WO | WO 92/06201 | 4/1992 |
| WO | WO 95/06128 | 2/1995 |

OTHER PUBLICATIONS

Hohn et al. Gene therapy in plants. proc. Natl. Acad. Sci. USA. Jul. 1999, vol. 96, pp. 8323.*
Forlani et al., Plant Sciences 85:9–15 (1992).
Forlani et al., Plant Physiol. 105:1107–1114 (1994).
Forlani et al., J. Plant Physiol., 150:369–375 (1997).
Abstract, Supplement to Plant Physiology, Ruff et al., No. 592, vol. 96, 1ˢᵗ Suppl. (1991).
Padgette et al., J. Biol. Chem., 266:22364 (1991).
Wan, Chun–Hua, Plant Regeneration, Cryopreservation and Genetic Transformation of Napiergrass, Dissertation; Univ. of Florida (1994).

* cited by examiner

Primary Examiner—Amy J. Nelson
Assistant Examiner—David H Kruse
(74) Attorney, Agent, or Firm—Connolly Bove Lodge & Hutz LLP

(57) ABSTRACT

The present invention relates to DNA molecules of plant origin encoding a modified 5-enolpyruvylshikimate-3-phosphate synthase (EPSPS) enzyme wherein the a first EPSPS coding sequence that normally encodes a threonine residue of a mature EPSPS sequence is modified to encode isoleucine of the mature EPSPS sequence, and a second EPSPS coding sequence that normally encodes a proline residue of a mature EPSPS sequence is modified to encode serine of the mature EPSPS sequence, wherein the first and second residues are respectively located at relatively positions 102 and 106 of a mature EPSPS sequence encoded by said DNA molecule; and the production of a transgenic plant resistant or tolerant to a herbicide of the phosphonomethylglycine family, e.g., glyphosate. The mutated enzyme, which substantially maintains the catalytic activity of the wild-type enzyme, allows for increased tolerance or tolerance of the plant to a herbicide of the phosphonomethylglycine family, and allows for the substantially normal growth or development of the plant, its organs, tissues or cells.

13 Claims, No Drawings

SEQUENCE LISTING

```
<160> NUMBER OF SEQ ID NOS:  15

<210> SEQ ID NO 1
<211> LENGTH: 1713
<212> TYPE: DNA
<213> ORGANISM: Zea mays

<400> SEQUENCE: 1
aatcaatttc acacaggaaa cagctatgac catgattacg aattcgggcc cgggcgcgtg      60
atccggcggc ggcagcggcg gcggcggtgc aggcgggtgc cgaggagatc gtgctgcagc     120
ccatcaagga gatctccggc accgtcaagc tgccggggtc caagtcgctt tccaaccgga     180
tcctcctact cgccgccctg tccgagggga caacagtggt tgataacctg ctgaacagtg     240
aggatgtcca ctacatgctc ggggccttga ggactcttgg tctctctgtc gaagcggaca     300
aagctgccaa aagagctgta gttgttggct gtggtggaaa gttcccagtt gaggatgcta     360
aagaggaagt gcagctcttc ttggggaatg ctggaactgc aatgcggcca ttgacagcag     420
ctgttactgc tgctggtgga aatgcaactt acgtgcttga tggagtacca agaatgaggg     480
agagacccat tggcgacttg gttgtcggat tgaagcagct tggtgcagat gttgattgtt     540
tccttggcac tgactgccca cctgttcgtg tcaatggaat cggagggcta cctggtggca     600
aggtcaagct gtctggctcc atcagcagtc agtacttgag tgccttgctg atggctgctc     660
ctttggctct tggggatgtg gagattgaaa tcattgataa attaatctcc attccgtacg     720
tcgaaatgac attgagattg atggagcgtt ttggtgtgaa agcagagcat tctgatagct     780
gggacagatt ctacattaag ggaggtcaaa aatacaagtc ccctaaaaat gcctatgttg     840
aaggtgatgc ctcaagcgca agctatttct tggctggtgc tgcaattact ggagggactg     900
```

```
tgactgtgga aggttgtggc accaccagtt tgcagggtga tgtgaagttt gctgaggtac      960
tggagatgat gggagcgaag gttacatgga ccgagactag cgtaactgtt actggcccac     1020
cgcgggagcc atttgggagg aaacacctca aggcgattga tgtcaacatg aacaagatgc     1080
ctgatgtcgc catgactctt gctgtggttg ccctctttgc cgatggcccg acagccatca     1140
gagacgtggc ttcctggaga gtaaaggaga ccgagaggat ggttgcgatc cggacggagc     1200
taaccaagct gggagcatct gttgaggaag gccggactac tgcatcatc acgccgccgg      1260 agaagctgaa cgtgacggcg atcgacacgt acgacgacca caggatggcc atggccttct     1320
cccttgccgc ctgtgccgag gtccccgtca ccatccggga ccctgggtgc acccggaaga     1380
ccttccccga ctacttcgat gtgctgagca ctttcgtcaa gaattaataa agcgtgcgat     1440
actaccacgc agcttgattg aagtgatagg cttgtgctga ggaaatacat ttcttttgtt     1500 ctgttttct ctttcacggg attaagtttt gagtctgtaa cgttagttgt ttgtagcaag      1560
tttctatttc ggatcttaag tttgtgcact gtaagccaaa tttcatttca agagtggttc     1620
gttggaataa taagaataat aaattacgtt tcagtgaaaa aaaaaaaaaa aaaaaaaaa      1680 aaaaaaaaaa aaaaaaaaaa aacccgggaa ttc                                  1713

<210> SEQ ID NO 2
<211> LENGTH: 1340
<212> TYPE: DNA
<213> ORGANISM: Zea mays
<220> FEATURE:
<221> NAME/KEY: CDS
<222> LOCATION: (6)..(1337)

<400> SEQUENCE: 2 ccatg gcc ggc gcc gag gag atc gtg ctg cag ccc atc aag gag atc tcc       50
      Ala Gly Ala Glu Glu Ile Val Leu Gln Pro Ile Lys Glu Ile Ser
        1               5                  10                  15 ggc acc gtc aag ctg ccg ggg tcc aag tcg ctt tcc aac cgg atc ctc         98
Gly Thr Val Lys Leu Pro Gly Ser Lys Ser Leu Ser Asn Arg Ile Leu
             20                  25                  30 cta ctc gcc gcc ctg tcc gag ggg aca aca gtg gtt gat aac ctg ctg        146
Leu Leu Ala Ala Leu Ser Glu Gly Thr Thr Val Val Asp Asn Leu Leu
         35                  40                  45 aac agt gag gat gtc cac tac atg ctc ggg gcc ttg agg act ctt ggt        194
Asn Ser Glu Asp Val His Tyr Met Leu Gly Ala Leu Arg Thr Leu Gly
     50                  55                  60 ctc tct gtc gaa gcg gac aaa gct gcc aaa aga gct gta gtt gtt ggc        242
Leu Ser Val Glu Ala Asp Lys Ala Ala Lys Arg Ala Val Val Val Gly
 65                  70                  75 tgt ggt gga aag ttc cca gtt gag gat gct aaa gag gaa gtg cag ctc        290
Cys Gly Gly Lys Phe Pro Val Glu Asp Ala Lys Glu Glu Val Gln Leu
 80                  85                  90                  95 ttc ttg ggg aat gct gga act gca atg cgg cca ttg aca gca gct gtt        338
Phe Leu Gly Asn Ala Gly Thr Ala Met Arg Pro Leu Thr Ala Ala Val
                100                 105                 110 act gct gct ggt gga aat gca act tac gtg ctt gat gga gta cca aga        386
Thr Ala Ala Gly Gly Asn Ala Thr Tyr Val Leu Asp Gly Val Pro Arg
            115                 120                 125 atg agg gag aga ccc att ggc gac ttg gtt gtc gga ttg aag cag ctt        434
Met Arg Glu Arg Pro Ile Gly Asp Leu Val Val Gly Leu Lys Gln Leu
        130                 135                 140 ggt gca gat gtt gat tgt ttc ctt ggc act gac tgc cca cct gtt cgt        482
Gly Ala Asp Val Asp Cys Phe Leu Gly Thr Asp Cys Pro Pro Val Arg
    145                 150                 155
```

```
gtc aat gga atc gga ggg cta cct ggt ggc aag gtc aag ctg tct ggc    530
Val Asn Gly Ile Gly Gly Leu Pro Gly Gly Lys Val Lys Leu Ser Gly
160             165                 170                 175 tcc atc agc agt cag tac ttg agt gcc ttg ctg atg gct gct cct ttg    578
Ser Ile Ser Ser Gln Tyr Leu Ser Ala Leu Leu Met Ala Ala Pro Leu
            180                 185                 190 gct ctt ggg gat gtg gag att gaa atc att gat aaa tta atc tcc att    626
Ala Leu Gly Asp Val Glu Ile Glu Ile Ile Asp Lys Leu Ile Ser Ile
        195                 200                 205 ccg tac gtc gaa atg aca ttg aga ttg atg gag cgt ttt ggt gtg aaa    674
Pro Tyr Val Glu Met Thr Leu Arg Leu Met Glu Arg Phe Gly Val Lys
    210                 215                 220 gca gag cat tct gat agc tgg gac aga ttc tac att aag gga ggt caa    722
Ala Glu His Ser Asp Ser Trp Asp Arg Phe Tyr Ile Lys Gly Gly Gln
225                 230                 235 aaa tac aag tcc cct aaa aat gcc tat gtt gaa ggt gat gcc tca agc    770
Lys Tyr Lys Ser Pro Lys Asn Ala Tyr Val Glu Gly Asp Ala Ser Ser
240                 245                 250                 255 gca agc tat ttc ttg gct ggt gct gca att act gga ggg act gtg act    818
Ala Ser Tyr Phe Leu Ala Gly Ala Ala Ile Thr Gly Gly Thr Val Thr
            260                 265                 270 gtg gaa ggt tgt ggc acc acc agt ttg cag ggt gat gtg aag ttt gct    866
Val Glu Gly Cys Gly Thr Thr Ser Leu Gln Gly Asp Val Lys Phe Ala
        275                 280                 285 gag gta ctg gag atg atg gga gcg aag gtt aca tgg acc gag act agc    914
Glu Val Leu Glu Met Met Gly Ala Lys Val Thr Trp Thr Glu Thr Ser
    290                 295                 300 gta act gtt act ggc cca ccg cgg gag cca ttt ggg agg aaa cac ctc    962
Val Thr Val Thr Gly Pro Pro Arg Glu Pro Phe Gly Arg Lys His Leu
305                 310                 315 aag gcg att gat gtc aac atg aac aag atg cct gat gtc gcc atg act   1010
Lys Ala Ile Asp Val Asn Met Asn Lys Met Pro Asp Val Ala Met Thr
320                 325                 330                 335 ctt gct gtg gtt gcc ctc ttt gcc gat ggc ccg aca gcc atc aga gac   1058
Leu Ala Val Val Ala Leu Phe Ala Asp Gly Pro Thr Ala Ile Arg Asp
            340                 345                 350 gtg gct tcc tgg aga gta aag gag acc gag agg atg gtt gcg atc cgg   1106
Val Ala Ser Trp Arg Val Lys Glu Thr Glu Arg Met Val Ala Ile Arg
        355                 360                 365 acg gag cta acc aag ctg gga gca tct gtt gag gaa ggg ccg gac tac   1154
Thr Glu Leu Thr Lys Leu Gly Ala Ser Val Glu Glu Gly Pro Asp Tyr
    370                 375                 380 tgc atc atc acg ccg ccg gag aag ctg aac gtg acg gcg atc gac acg   1202
Cys Ile Ile Thr Pro Pro Glu Lys Leu Asn Val Thr Ala Ile Asp Thr
385                 390                 395 tac gac gac cac agg atg gcc atg gcc ttc tcc ctt gcc gcc tgt gcc   1250
Tyr Asp Asp His Arg Met Ala Met Ala Phe Ser Leu Ala Ala Cys Ala
400                 405                 410                 415 gag gtc ccc gtc acc atc cgg gac cct ggg tgc acc cgg aag acc ttc   1298
Glu Val Pro Val Thr Ile Arg Asp Pro Gly Cys Thr Arg Lys Thr Phe
            420                 425                 430 ccc gac tac ttc gat gtg ctg agc act ttc gtc aag aat taa           1340
Pro Asp Tyr Phe Asp Val Leu Ser Thr Phe Val Lys Asn
        435                 440
```

<210> SEQ ID NO 3
<211> LENGTH: 444
<212> TYPE: PRT
<213> ORGANISM: Zea mays

-continued

```
<400> SEQUENCE: 3

Ala Gly Ala Glu Glu Ile Val Leu Gln Pro Ile Lys Glu Ile Ser Gly
 1               5                  10                  15

Thr Val Lys Leu Pro Gly Ser Lys Ser Leu Ser Asn Arg Ile Leu Leu
             20                  25                  30

Leu Ala Ala Leu Ser Glu Gly Thr Thr Val Val Asp Asn Leu Leu Asn
         35                  40                  45

Ser Glu Asp Val His Tyr Met Leu Gly Ala Leu Arg Thr Leu Gly Leu
     50                  55                  60

Ser Val Glu Ala Asp Lys Ala Ala Lys Arg Ala Val Val Val Gly Cys
 65                  70                  75                  80

Gly Gly Lys Phe Pro Val Glu Asp Ala Lys Glu Glu Val Gln Leu Phe
                 85                  90                  95

Leu Gly Asn Ala Gly Thr Ala Met Arg Pro Leu Thr Ala Ala Val Thr
            100                 105                 110

Ala Ala Gly Gly Asn Ala Thr Tyr Val Leu Asp Gly Val Pro Arg Met
        115                 120                 125

Arg Glu Arg Pro Ile Gly Asp Leu Val Val Gly Leu Lys Gln Leu Gly
130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Ile Asp Lys Leu Ile Ser Ile Pro
        195                 200                 205

Tyr Val Glu Met Thr Leu Arg Leu Met Glu Arg Phe Gly Val Lys Ala
    210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Thr Val Thr Val
            260                 265                 270

Glu Gly Cys Gly Thr Thr Ser Leu Gln Gly Asp Val Lys Phe Ala Glu
        275                 280                 285

Val Leu Glu Met Met Gly Ala Lys Val Thr Trp Thr Glu Thr Ser Val
    290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
        355                 360                 365

Glu Leu Thr Lys Leu Gly Ala Ser Val Glu Glu Gly Pro Asp Tyr Cys
    370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415
```

```
Val Pro Val Thr Ile Arg Asp Pro Gly Cys Thr Arg Lys Thr Phe Pro
            420                 425                 430
Asp Tyr Phe Asp Val Leu Ser Thr Phe Val Lys Asn
        435                 440

<210> SEQ ID NO 4
<211> LENGTH: 1340
<212> TYPE: DNA
<213> ORGANISM: Zea mays
<220> FEATURE:
<221> NAME/KEY: CDS
<222> LOCATION: (6)..(1337)

<400> SEQUENCE: 4 ccatg gcc ggc gcc gag gag atc gtg ctg cag ccc atc aag gag atc tcc        50
      Ala Gly Ala Glu Glu Ile Val Leu Gln Pro Ile Lys Glu Ile Ser
      1               5                   10                  15 ggc acc gtc aag ctg ccg ggg tcc aag tcg ctt tcc aac cgg atc ctc          98
Gly Thr Val Lys Leu Pro Gly Ser Lys Ser Leu Ser Asn Arg Ile Leu
            20                  25                  30 cta ctc gcc gcc ctg tcc gag ggg aca aca gtg gtt gat aac ctg ctg         146
Leu Leu Ala Ala Leu Ser Glu Gly Thr Thr Val Val Asp Asn Leu Leu
        35                  40                  45 aac agt gag gat gtc cac tac atg ctc ggg gcc ttg agg act ctt ggt         194
Asn Ser Glu Asp Val His Tyr Met Leu Gly Ala Leu Arg Thr Leu Gly
    50                  55                  60 ctc tct gtc gaa gcg gac aaa gct gcc aaa aga gct gta gtt gtt ggc         242
Leu Ser Val Glu Ala Asp Lys Ala Ala Lys Arg Ala Val Val Val Gly
65                  70                  75 tgt ggt gga aag ttc cca gtt gag gat gct aaa gag gaa gtg cag ctc         290
Cys Gly Gly Lys Phe Pro Val Glu Asp Ala Lys Glu Glu Val Gln Leu
80                  85                  90                  95 ttc ttg ggg aat gct gga atc gca atg cgg tcc ttg aca gca gct gtt         338
Phe Leu Gly Asn Ala Gly Ile Ala Met Arg Ser Leu Thr Ala Ala Val
                100                 105                 110 act gct gct ggt gga aat gca act tac gtg ctt gat gga gta cca aga         386
Thr Ala Ala Gly Gly Asn Ala Thr Tyr Val Leu Asp Gly Val Pro Arg
            115                 120                 125 atg agg gag aga ccc att ggc gac ttg gtt gtc gga ttg aag cag ctt         434
Met Arg Glu Arg Pro Ile Gly Asp Leu Val Val Gly Leu Lys Gln Leu
        130                 135                 140 ggt gca gat gtt gat tgt ttc ctt ggc act gac tgc cca cct gtt cgt         482
Gly Ala Asp Val Asp Cys Phe Leu Gly Thr Asp Cys Pro Pro Val Arg
    145                 150                 155 gtc aat gga atc gga ggg cta cct ggt ggc aag gtc aag ctg tct ggc         530
Val Asn Gly Ile Gly Gly Leu Pro Gly Gly Lys Val Lys Leu Ser Gly
160                 165                 170                 175 tcc atc agc agt cag tac ttg agt gcc ttg ctg atg gct gct cct ttg         578
Ser Ile Ser Ser Gln Tyr Leu Ser Ala Leu Leu Met Ala Ala Pro Leu
                180                 185                 190 gct ctt ggg gat gtg gag att gaa atc att gat aaa tta atc tcc att         626
Ala Leu Gly Asp Val Glu Ile Glu Ile Ile Asp Lys Leu Ile Ser Ile
            195                 200                 205 ccg tac gtc gaa atg aca ttg aga ttg atg gag cgt ttt ggt gtg aaa         674
Pro Tyr Val Glu Met Thr Leu Arg Leu Met Glu Arg Phe Gly Val Lys
        210                 215                 220 gca gag cat tct gat agc tgg gac aga ttc tac att aag gga ggt caa         722
Ala Glu His Ser Asp Ser Trp Asp Arg Phe Tyr Ile Lys Gly Gly Gln
    225                 230                 235 aaa tac aag tcc cct aaa aat gcc tat gtt gaa ggt gat gcc tca agc         770
```

```
                                                              -continued

Lys Tyr Lys Ser Pro Lys Asn Ala Tyr Val Glu Gly Asp Ala Ser Ser
240                 245                 250                 255 gca agc tat ttc ttg gct ggt gct gca att act gga ggg act gtg act       818
Ala Ser Tyr Phe Leu Ala Gly Ala Ala Ile Thr Gly Gly Thr Val Thr
                    260                 265                 270 gtg gaa ggt tgt ggc acc acc agt ttg cag ggt gat gtg aag ttt gct       866
Val Glu Gly Cys Gly Thr Thr Ser Leu Gln Gly Asp Val Lys Phe Ala
                275                 280                 285 gag gta ctg gag atg atg gga gcg aag gtt aca tgg acc gag act agc       914
Glu Val Leu Glu Met Met Gly Ala Lys Val Thr Trp Thr Glu Thr Ser
            290                 295                 300 gta act gtt act ggc cca ccg cgg gag cca ttt ggg agg aaa cac ctc       962
Val Thr Val Thr Gly Pro Pro Arg Glu Pro Phe Gly Arg Lys His Leu
        305                 310                 315 aag gcg att gat gtc aac atg aac aag atg cct gat gtc gcc atg act      1010
Lys Ala Ile Asp Val Asn Met Asn Lys Met Pro Asp Val Ala Met Thr
320                 325                 330                 335 ctt gct gtg gtt gcc ctc ttt gcc gat ggc ccg aca gcc atc aga gac      1058
Leu Ala Val Val Ala Leu Phe Ala Asp Gly Pro Thr Ala Ile Arg Asp
                    340                 345                 350 gtg gct tcc tgg aga gta aag gag acc gag agg atg gtt gcg atc cgg      1106
Val Ala Ser Trp Arg Val Lys Glu Thr Glu Arg Met Val Ala Ile Arg
                355                 360                 365 acg gag cta acc aag ctg gga gca tct gtt gag gaa ggg ccg gac tac      1154
Thr Glu Leu Thr Lys Leu Gly Ala Ser Val Glu Glu Gly Pro Asp Tyr
            370                 375                 380 tgc atc atc acg ccg ccg gag aag ctg aac gtg acg gcg atc gac acg      1202
Cys Ile Ile Thr Pro Pro Glu Lys Leu Asn Val Thr Ala Ile Asp Thr
        385                 390                 395 tac gac gac cac agg atg gcg atg gcc ttc tcc ctt gcc gcc tgt gcc      1250
Tyr Asp Asp His Arg Met Ala Met Ala Phe Ser Leu Ala Ala Cys Ala
400                 405                 410                 415 gag gtc ccc gtc acc atc cgg gac cct ggg tgc acc cgg aag acc ttc      1298
Glu Val Pro Val Thr Ile Arg Asp Pro Gly Cys Thr Arg Lys Thr Phe
                    420                 425                 430 ccc gac tac ttc gat gtg ctg agc act ttc gtc aag aat taa              1340
Pro Asp Tyr Phe Asp Val Leu Ser Thr Phe Val Lys Asn
                435                 440

<210> SEQ ID NO 5
<211> LENGTH: 444
<212> TYPE: PRT
<213> ORGANISM: Zea mays

<400> SEQUENCE: 5

Ala Gly Ala Glu Glu Ile Val Leu Gln Pro Ile Lys Glu Ile Ser Gly
 1               5                  10                  15

Thr Val Lys Leu Pro Gly Ser Lys Ser Leu Ser Asn Arg Ile Leu Leu
                20                  25                  30

Leu Ala Ala Leu Ser Glu Gly Thr Thr Val Val Asp Asn Leu Leu Asn
            35                  40                  45

Ser Glu Asp Val His Tyr Met Leu Gly Ala Leu Arg Thr Leu Gly Leu
        50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Glu Val Gln Leu Phe
                85                  90                  95

Leu Gly Asn Ala Gly Ile Ala Met Arg Ser Leu Thr Ala Ala Val Thr
            100                 105                 110
```

```
Ala Ala Gly Gly Asn Ala Thr Tyr Val Leu Asp Gly Val Pro Arg Met
            115                 120                 125
Arg Glu Arg Pro Ile Gly Asp Leu Val Val Gly Leu Lys Gln Leu Gly
        130                 135                 140
Ala Asp Val Asp Cys Phe Leu Gly Thr Asp Cys Pro Pro Val Arg Val
145                 150                 155                 160
Asn Gly Ile Gly Gly Leu Pro Gly Gly Lys Val Lys Leu Ser Gly Ser
                165                 170                 175
Ile Ser Ser Gln Tyr Leu Ser Ala Leu Leu Met Ala Ala Pro Leu Ala
            180                 185                 190
Leu Gly Asp Val Glu Ile Glu Ile Ile Asp Lys Leu Ile Ser Ile Pro
        195                 200                 205
Tyr Val Glu Met Thr Leu Arg Leu Met Glu Arg Phe Gly Val Lys Ala
        210                 215                 220
Glu His Ser Asp Ser Trp Asp Arg Phe Tyr Ile Lys Gly Gly Gln Lys
225                 230                 235                 240
Tyr Lys Ser Pro Lys Asn Ala Tyr Val Glu Gly Asp Ala Ser Ser Ala
                245                 250                 255
Ser Tyr Phe Leu Ala Gly Ala Ile Thr Gly Gly Thr Val Thr Val
            260                 265                 270
Glu Gly Cys Gly Thr Thr Ser Leu Gln Gly Asp Val Lys Phe Ala Glu
        275                 280                 285
Val Leu Glu Met Met Gly Ala Lys Val Thr Trp Thr Glu Thr Ser Val
        290                 295                 300
Thr Val Thr Gly Pro Pro Arg Glu Pro Phe Gly Arg Lys His Leu Lys
305                 310                 315                 320
Ala Ile Asp Val Asn Met Asn Lys Met Pro Asp Val Ala Met Thr Leu
                325                 330                 335
Ala Val Val Ala Leu Phe Ala Asp Gly Pro Thr Ala Ile Arg Asp Val
            340                 345                 350
Ala Ser Trp Arg Val Lys Glu Thr Glu Arg Met Val Ala Ile Arg Thr
        355                 360                 365
Glu Leu Thr Lys Leu Gly Ala Ser Val Glu Glu Gly Pro Asp Tyr Cys
        370                 375                 380
Ile Ile Thr Pro Pro Glu Lys Leu Asn Val Thr Ala Ile Asp Thr Tyr
385                 390                 395                 400
Asp Asp His Arg Met Ala Met Ala Phe Ser Leu Ala Ala Cys Ala Glu
                405                 410                 415
Val Pro Val Thr Ile Arg Asp Pro Gly Cys Thr Arg Lys Thr Phe Pro
            420                 425                 430
Asp Tyr Phe Asp Val Leu Ser Thr Phe Val Lys Asn
        435                 440

<210> SEQ ID NO 6
<211> LENGTH: 20
<212> TYPE: DNA
<213> ORGANISM: Zea mays

<400> SEQUENCE: 6
gctctgctca tgtctgctcc                                              20

<210> SEQ ID NO 7
<211> LENGTH: 20
<212> TYPE: DNA
<213> ORGANISM: Zea mays
```

<400> SEQUENCE: 7
gcccgccctt gacaaagaaa                                           20

<210> SEQ ID NO 8
<211> LENGTH: 38
<212> TYPE: DNA
<213> ORGANISM: Zea mays

<400> SEQUENCE: 8
aattaagctc tagagtcgac ctgcaggcat gcaagctt                       38

<210> SEQ ID NO 9
<211> LENGTH: 41
<212> TYPE: DNA
<213> ORGANISM: Zea mays

<400> SEQUENCE: 9
gagccgagct ccatggccgg cgccgaggag atcgtgctgc a                   41

<210> SEQ ID NO 10
<211> LENGTH: 37
<212> TYPE: DNA
<213> ORGANISM: Zea mays

<400> SEQUENCE: 10
gcacgatctc ctcggcgccg gccatggagc tcggctc                        37

<210> SEQ ID NO 11
<211> LENGTH: 25
<212> TYPE: DNA
<213> ORGANISM: Zea mays

<400> SEQUENCE: 11
ccacaggatg gcgatggcct tctcc                                     25

<210> SEQ ID NO 12
<211> LENGTH: 33
<212> TYPE: DNA
<213> ORGANISM: Zea mays

<400> SEQUENCE: 12
gaatgctgga atcgcaatgc ggccattgac agc                            33

<210> SEQ ID NO 13
<211> LENGTH: 33
<212> TYPE: DNA
<213> ORGANISM: Zea mays

<400> SEQUENCE: 13
gaatgctgga actgcaatgc ggtccttgac agc                            33

<210> SEQ ID NO 14
<211> LENGTH: 34
<212> TYPE: DNA
<213> ORGANISM: Zea mays

<400> SEQUENCE: 14
cttggggaat gctgccatcg caatgcggcc attg                           34

<210> SEQ ID NO 15
<211> LENGTH: 36
<212> TYPE: DNA

-continued

```
<213> ORGANISM: Zea mays

<400> SEQUENCE: 15
ggggaatgct ggaatcgcaa tgcggtcctt gacagc                              36
```

US 6,566,587 B1

MUTATED 5-ENOLPYRUVYLSHIKIMATE-3-PHOSPHATE SYNTHASE, GENE CODING FOR SAID PROTEIN AND TRANSFORMED PLANTS CONTAINING SAID GENE

FIELD OF THE INVENTION

The present invention relates to a new 5-enolpyruvylshikimate-3-phosphate synthase (or EPSPS) which displays increased tolerance with respect to herbicides which are competitive inhibitors with respect to phosphoenolpyruvate (PEP) of EPSPS activity. This more tolerant EPSP synthase possesses at least one "threonine by isoleucine" substitution. The invention also relates to a gene coding for such a protein, to plant cells transformed by chimeric gene constructions containing this gene, to the plants regenerated from these cells and also to the plants originating from crossing using these transformed plants.

BACKGROUND OF THE INVENTION

Glyphosate, sulfosate and fosametine are broad-spectrum systemic herbicides of the phosphonomethylglycine family. They act essentially as competitive inhibitors of 5-enolpyruvylshikimate-3-phosphate synthase (EC 2.5.1.19) or EPSPS with respect to the PEP (phosphoenolpyruvate). After their application to the plant, they are translocated in the plant where they accumulate in the rapidly growing parts, in particular the cauline and root spices, causing damage to the point of destruction of sensitive plants.

Plastid EPSPS, the main target of these products, is an enzyme of the pathway of biosynthesis of aromatic amino acids, which is encoded by one or more nuclear genes and synthesized in the form of a cytoplasmic precursor, then imported into the plastids where it accumulates in its mature form.

The tolerance of plants to glyphosate and to products of the family is obtained by stable introduction into their genome of an EPSPS gene, of plant or bacterial origin, which is mutated or otherwise in respect of the characteristics of inhibition by glyphosate of the product of this gene. In view of the mode of action of glyphosate and the degree of tolerance to glyphosate of the product of the genes which are used, it is advantageous to be able to express the product of the translation of this gene so as enable it to be accumulated in substantial amounts in the plastids.

It is known, for example from U.S. Pat. No. 4,535,060, to confer on a plant a tolerance to a herbicide of the above type, especially N-phosphonomethylglycine or glyphosate, by introducing into the genome of plants a gene coding for an EPSPS carrying at least one mutation that makes this enzyme more resistant to its competitive inhibitor (glyphosate) after localization of the enzyme in the plastid compartment. These techniques, however, need to be improved in order to obtain greater reliability in the use of these plants under agricultural conditions.

SUMMARY OF THE INVENTION

In the present description, "plant" is understood to mean any differentiated multicellular organism capable of photosynthesis, and "plant cell" is understood to mean any cell originating from a plant and capable of constituting undifferentiated tissues such as calluses or differentiated tissues such as embryos or plant parts or seeds.

The subject of the present invention is the production of transformed plants having increased tolerance to herbicides of the phosphonomethylglycine family, by regeneration of cells transformed by means of new chimeric genes containing a gene for tolerance to these herbicides.

The subject of the invention is also a chimeric gene for conferring on plants increased tolerance with respect to a herbicide having EPSPS as its target, comprising, in the direction of transcription: a promoter region, optionally a transit peptide region, a sequence of a gene coding for a glyphosate tolerance enzyme and an untranslated polyadenylation signal region at the 3' end, characterized in that the glyphosate tolerance gene contains, relative to the gene from which it is derived, a "threonine 102 by isoleucine" substitution in the "aroA" (EPSPS) region. Preferably, it comprises, in addition, in the same region, a "proline 106 by serine" substitution. These substitutions can be introduced or be present in an EPSPS sequence of any origin, in particular of plant, bacterial, algal or fungal origin.

DESCRIPTION OF PREFERRED EMBODIMENTS

The transit peptides which can be used in the transit peptide region can be, known per se, of plant origin, for example originating from maize, sunflower, pea, tobacco or the like. The first and the second transit peptide can be identical, similar or different. They can, in addition, each comprise one or more transit peptide units according to European Patent Application AP 0 508 909. It is the role of this characteristic region to permit the release of a mature and native protein, and especially the above mutated EPSPS, with maximum efficacy in the plasmid compartment.

The promoter region of the chimeric gene according to the invention may be advantageously composed of at least one gene promoter or promoter fragment which is expressed naturally in plants (tubulin, introns, actin, histone).

The untranslated transcription termination signal region at the 3' end of the chimeric gene may be of any origin, for example of bacterial origin, such as that of the nopaline synthase gene, or of plant origin, such as that of the *Arabidopsis thaliana* histone H4A748 gene according to the European Patent Application (European Application 633 317).

The chimeric gene according to the invention can comprise, in addition to the essential portions above, at least one untranslated intermediate (linker) region, which can be located between the different transcribed regions described above. This intermediate region can be of any origin, for example of bacterial, viral or plant origin.

Isolation of a cDNA coding for a maize EPSPS:

The different steps which led to the obtaining of maize EPSPS cDNA, which served as substrate for the introduction of the two mutations, are described below. All the operations described below are given by way of example, and correspond to a choice made from among the different methods available for arriving at the same result. This choice has no effect on the quality of the result, and consequently any suitable method may be used by a person skilled in the art to arrive at the same result. Most of the methods of engineering of DNA fragments are described in "Current Protocols in Molecular Biology" Volumes 1 and 2, Ausubel F. M. et al., published by Greene Publishing Associates and Wiley-Interscience (1989) (hereinafter, references to protocols described in this work will be designated "ref. CPMB"). The operations relating to DNA which were performed according to the protocols described in this work are especially the following: ligation of DNA fragments, treatment with Klenow DNA polymerase and T4 DNA polymerase, preparation of plasmid and of bacteriophage λ DNA, either as a minipreparation or as a maxipreparation, and DNA and RNA analyses according to the Southern and Northern techniques, respectively. Other methods described in this work were followed, and only significant modifications or additions to these protocols have been described below.

EXAMPLE 1

1. Obtaining of an *Arabidopsis thaliana* EPSPS fragment
   a) Two 20-mer oligonucleotides of respective sequences:

5'-GCTCTGCTCATGTCTGCTCC-3'   (SEQ ID NO:6)

5'-GCCCGCCCTTGACAAAGAAA-3'   (SEQ ID NO:7)

were synthesized from the sequence of an *Arabidopsis thaliana* EPSPS gene (Klee H. J. et al. (1987) Mol. Gen. Genet., 210, 437–422). These two oligonucleotides are at positions 1523 to 1543 and 1737 to 1717, respectively, of the published sequence, and in opposite orientations.
   b) *Arabidopsis thaliana* (var. *columbia*) total DNA was obtained from Clontech (catalogue reference: 6970-1).
   c) 50 nanograms (ng) of DNA are mixed with 300 ng of each of the oligonucleotides and subjected to 35 amplification cycles with a Perkin-Elmer 9600 apparatus, under the conditions of standard medium for amplification which are recommended by the supplier. The resulting 204-bp fragment constitutes the *Arabidopsis thaliana* EPSPS fragment.

2. Construction of a library of a cDNA from a BMS maize cell line
   a) 5 g of filtered cells are ground in liquid nitrogen, and the total nucleic acids are extracted according to the method described by Shure et al. with the following modifications:
      the pH of the lysis buffer is adjusted to pH 9.0;
      after precipitation with isopropanol, the pellet is taken up in water and, after dissolution, adjusted to 2.5 M LiCl. After incubation for 12 h at ° C., the pellet from centrifugation for 15 min at 30,000 g at 4° C. is resolubilized. The LiCl precipitation step is then repeated. The resolubilized pellet constitutes the RNA fraction of the total nucleic acids.
   b) The poly(A)$^+$ RNA fraction of the RNA fraction is obtained by chromatography on an oligo(dT)-cellulose column as described in "Current Protocols in Molecular Biology".
   c) Synthesis of double-stranded cDNA having a synthetic EcoRI end: this is carried out according to the protocol of the supplier of the different reagents needed for this synthesis in the form of a kit: the "copy kit" from the company In Vitrogen.
   Two single-stranded and partially complementary oligonucleotides of respective sequences:
   5'-AATTCCCGGG-3'
   5'-CCCGGG-3' (the latter being phosphorylated)
   are ligated with the blunt-ended double-stranded cDNAs.
   This ligation of the adaptors results in the creation of SmaI sites attached to the double-stranded cDNAs and EcoRI sites in cohesive form at each end of the double-stranded cDNAs.
   d) Creation of the library:
   The cDNAs possessing the artificial cohesive EcoRI sites at their ends are ligated with bacteriophage λgt10 cDNA which has been cut with EcoRI and dephosphorylated according to the protocol of the supplier New England Biolabs.

An aliquot of the ligation reaction was encapsidated in vitro with encapsidation extracts, namely Gigapack Gold, according to the supplier's instructions; this library was titrated using the bacterium *E. coli* C600hfl. The library thereby obtained is amplified and stored according to the instructions of the same supplier, and constitutes the BMS maize cell suspension cDNA library.

3. Screening of the BMS maize cell suspension cDNA library with the *Arabidopsis thaliana* EPSP probe The protocol followed is that of "Current Protocols in Molecular Biology" Volumes 1 and 2, Ausubel F. M. et al., published by Greene Publishing Associates and Wiley-Interscience (1989) (CPMB). Briefly, approximately $10^6$ recombinant phages are plated out on LB dishes at an average density of 100 phages/cm$^2$. The lytic plaques are replicated in duplicate on Amersham Hybond N membranes.

The DNA was fixed to the filters by 1600 kJ UV treatment (Stratagene Stratalinker). The filters were prehybridized in 6×SSC/0.1%SDS/0.25 skimmed milk for 2 h at 65° C. The *Arabidopsis thaliana* EPSPS probe was labelled with [$^{32}$P] dCTP by random priming according to the supplier's instructions (Pharmacia Ready to Go kit). The specific activity obtained is of the order of $10^8$ cpm per µg of fragment. After denaturation for 5 min at 100° C., the probe is added to the prehybridization medium and hybridization is continued for 14 hours at 55° C. The filters are fluorographed for 48 h at −80° C. with Kodak XAR5 film and Amersham Hyperscreen RPN enhancing screens. Alignment of the positive spots on the filter with the dishes from which they originate enables zones corresponding to the phages displaying a positive hybridization response with the *Arabidopsis thaliana* EPSPS probe to be picked out from the dish. This step of plating out, transfer, hybridization and recovery is repeated until all the spots in the dish of the successively purified phages prove 100% positive in hybridization. An independent plaque of phage lysis is then picked out in diluent λ medium (Tris-Cl pH 7.5; 10 mM MgSO$_4$; 0.1M NaCl; 0.1% gelatin); these phages in solution constitute the EPSP-positive clones of the BMS maize cell suspension.

4. Preparation and analysis of the DNA of the EPSP clones of the BMS maize cell suspension Approximately 5×10$^8$ phages are added to 20 ml of C600hfl bacteria at an OD$_{600nm}$ value of 2/ml and incubated for 15 minutes at 37° C. This suspension is then diluted in 200 ml of bacterial growth medium in a 1-l Erlenmeyer and stirred in a rotary stirrer at 250 rpm. Lysis is noted when the medium clarifies, corresponding to the lysis of the turbid bacteria, and takes place after approximately 4 h of stirring. This supernatant is then treated as described in "Current Protocols in Molecular Biology". The DNA obtained corresponds to the EPSP clones of the BMS maize cell suspension.

One to two µg of this DNA are cut with EcoRI and separated on 0.8% LGTA/TBE agarose gel (ref. CPMB). A final verification consists in checking that the purified DNA does indeed display a hybridization signal with the *Arabidopsis thaliana* EPSPS probe. After electrophoresis, the DNA fragments are transferred onto Amersham Hybond N membranes according to the protocol of Southern described in "Current Protocols in Molecular Biology". The filter is hybridized with the *Arabidopsis thaliana* EPSPS probe according to the conditions described in section 3 above. The clone displaying a hybridization signal with the *Arabidopsis thaliana* EPSPS probe and containing the longest EcoRI fragment has a size estimated on gel as approximately 1.7 kbp.

5. Obtaining of the clone pRPA-ML-711

Ten μg of the phage clone containing the 1.7-kbp insert are digested with EcoRI and separated on 0.8% LGTA/TBE agarose gel (ref. CPMB). The gel fragment containing the 1.7-kbp insert is excised from the gel by BET staining, and the fragment is treated with β-agarase according to the protocol of the supplier, New England Biolabs. The purified DNA of the 1.7-kbp fragment is ligated at 12° C. for 14 h with the DNA of plasmid pUC 19 (New England Biolabs) cut with EcoRI according to the ligation protocol described in "Current Protocols in Molecular Biology". Two μl of the above ligation mixture are used for the transformation of an aliquot of electrocompetent E. coli DH10B; transformation is accomplished by electroporation using the following conditions: the mixture of competent bacteria and ligation medium is introduced into an electroporation cell of thickness 0.2 cm (Biorad) previously cooled to 0° C. The physical conditions of the electroporation using an electroporator made by Biorad are 2500 volts, 25 μF and 200 Ω. Under these conditions, the mean discharge time of the condenser is of the order of 4.2 milliseconds. The bacteria are then taken up in 1 ml of SOC medium (ref. CPMB) and stirred for 1 hour at 200 rpm on a rotary stirrer in 15-ml Corning tubes. After plating out on LB/agar medium supplemented with 100 μg/ml of carbenicillin, minipreparations of the bacterial clones which have grown after one night at 37° C. are produced according to the protocol described in "Current Protocols in Molecular Biology". After digestion of the DNA with EcoRI and separation by electrophoresis on 0.8% LGTA/TBE agarose gel (ref. CPMB), the clones possessing a 1.7-kbp insert are retained. A final verification consists in checking that the purified DNA does indeed display a hybridization signal with the Arabidopsis thaliana EPSPS probe. After electrophoresis, the DNA fragments are transferred onto Amersham Hybond N membranes according to the protocol of Southern described in "Current Protocols in Molecular Biology". The filter is hybridized with the Arabidopsis thaliana EPSPS probe according to the conditions described in section 3 above. The plasmid clone possessing a 1.7-kbp insert and hybridizing with the Arabidopsis thaliana EPSPS probe was prepared on a larger scale, and the DNA resulting from the lysis of the bacteria was purified on a CaCl gradient as described in "Current Protocols in Molecular Biology". The purified DNA was partially sequenced with a Pharmacia kit according to the supplier's instructions and using as primers the M13 direct and reverse universal primers ordered from the same supplier. The partial sequence produced covers approximately 0.5 kbp. The derived amino acid sequence in the region of the mature protein (approximately 50 amino acid residues) displays 100% identity with the corresponding amino sequence of mature maize EPSPS described in American patent U.S. Pat. No. 4,971,908. This clone, corresponding to a 1.7-kbp EcoRI fragment of the EPSP DNA of the BMS maize cell suspension, was designated pRPA-ML-711. The complete sequence of this clone was determined on both strands using the protocol of the Pharmacia kit and synthesizing complementary oligonucleotides and those of the opposite orientation every 250 bp approximately. The complete sequence obtained of this 1713-bp clone is presented in SEQ ID No. 1.

6. Obtaining of the clone pRPA-ML-715

Analysis of the sequence of the clone pRPA-ML-711, and especially comparison of the derived amino acid sequence with that of maize, shows a sequence extension of 92 bp upstream of the GCG codon coding for the NH$_2$-terminal alanine of the mature portion of maize EPSPS (American patent U.S. Pat. No. 4,971,908). Similarly, an extension of 288 bp downstream of the AAT codon coding for the COOH-terminal asparagine of the mature portion of maize EPSPS (American patent U.S. Pat. No. 4,971,908) is observed. These two portions could correspond, in the case of the NH$_2$-terminal extension to a portion of the sequence of a transit peptide for plastid localization, and, in the case of the COOH-terminal extension, to the untranslated 3' region of the cDNA.

In order to obtain a cDNA coding for the mature portion of the maize EPSPS cDNA, as described in U.S. Pat. No. 4,971,908, the following operations were carried out:

a) Removal of the untranslated 3' region: construction of pRPA-ML-712:

The clone pRPA-ML-711 was cut with the restriction enzyme AseI, and the ends resulting from this cleavage were rendered blunt by treatment with the Klenow fragment of DNA polymerase I according to the protocol described in CPMB. A cleavage with the restriction enzyme SacII was then performed. The DNA resulting from these operations was separated by electrophoresis on 1% LGTA/TBE agarose gel (ref. CPMB).

The gel fragment containing the 0.4-kbp "AseI-blunt ends/SacII" insert was excised from the gel and purified according to the protocol described in section 5 above. The DNA of the clone pRPA-ML-711 was out with the restriction enzyme HindIII at the HindIII site located in the polylinker of the cloning vector pUC19, and the ends resulting from this cleavage were rendered blunt by treatment with the Klenow fragment of DNA polymerase I. A cleavage with the restriction enzyme SacII was then performed. The DNA resulting from these manipulations was separated by electrophoresis on 0.7% LGTA/TBE agarose gel (ref. CPMB).

The gel fragment containing the approximately 3.7-kbp HindIII-blunt ends/SacII insert was excised from the gel and purified according to the protocol described in section 5 above.

The two inserts were ligated, and 2 μl of the ligation mixture were used to transform E. coli DH10B as described above in section 5.

The plasmid DNA content of different clones was analysed according to the procedure described for pRPA-ML-711. One of the plasmid clones selected contains an approximately 1.45-kbp EcoRI-HindIII insert. The sequence of the terminal ends of this clone reveals that the 5' end of the insert corresponds exactly to the corresponding end of pRPA-ML-711, and that the 3'-terminal end possesses the following sequence:

"5'- . . . . AATTAAGCTCTAGAGTCGACCTGCAGGCATGCA-
    AGCTT-3'".                                   (SEQ ID NO:8)

The underlined sequence corresponds to the codon of the COOH-terminal amino acid asparagine, the next codon corresponding to the translation stop codon. The nucleotides downstream correspond to sequence elements of the pUC19 polylinker. This clone comprising the pRPA-ML-711 sequence up to the translation termination site of mature maize EPSPS and followed by sequences of the pUC 19 polylinker up to the HindIII site was designated pRPA-ML-712.

b) Modification of the 5' end of pRPA-ML-712: construction of pRPA-ML-715:

The clone pRPA-ML-712 was cut with the restriction enzymes PstI and HindIII. The DNA resulting from these manipulations was separated by electrophoresis on 0.8% LGTA/TBE agarose gel (ref. CPMB). The gel fragment containing the 1.3-kbp PstI-EcoRI insert was excised from the gel and purified according to the protocol described in section 5 above. This insert was ligated in the presence of an equimolecular amount of each of the two partially complementary oligonucleotides of sequence:

Oligo 1: 5'-GAGCCGAGCTCCATGGCCGGCGCCGAG-
GAGATCGTGCTGCA-3' (SEQ ID NO:9)

Oligo 2: 5'-GCACGATCTCCTCGGCGCCGGCCATG-
GAGCTCGGCTC-3' (SEQ ID NO:10)

as well as in the presence of plasmid pUC19 DNA digested with the restriction enzymes BamHI and HindIII.

Two μl of the ligation mixture were used to transform E. coli DH10B as described above in section 5. After analysis of the plasmid DNA content of different clones according to the procedure described above in section 5, one of the clones possessing an approximately 1.3-kbp insert was retained for subsequent analyses. The sequence of the 5'-terminal end of the selected clone reveals that the DNA sequence in this region is the following: sequence of the pUC19 polylinker from the EcoRI to the BamHI sites, followed by the sequence of the oligonucleotides used in the cloning, followed by the remainder of the sequence present in pRPA-ML-712. This clone was designated pRPA-ML-713. This clone possesses a methionine ATG codon included in an NcoI site upstream of the N-terminal alanine codon of mature EPSP synthase. Furthermore, the alanine and glycine codons of the N-terminal end have been preserved, but modified on the third variable base: initial GCGGGT gives modified GCCGGC.

The clone pRPA-ML-713 was out with the restriction enzyme HindIII, and the ends of this cleavage were rendered blunt by treatment with the Klenow fragment of DNA polymerase I. A cleavage with restriction enzyme SacI was then performed. The DNA resulting from these manipulations was separated by electrophoresis on 0.8% LGTA/TBE agarose gel (ref. CPMB). The gel fragment containing the 1.3-kbp "HindIII-blunt ends/SacI" insert was excised from the gel and purified according to the protocol described in section 5 above. This insert was ligated in the presence of plasmid pUC19 DNA digested with restriction enzyme XbaI, and the ends of this cleavage were rendered blunt by treatment with the Klenow fragment of DNA polymerase I. A cleavage with the restriction enzyme SacI was then performed. Two μl of the ligation mixture were used to transform E. coli DH10B as described above in section 5. After analysis of the plasmid DNA content of different clones according to the procedure described above in section 5, one of the clones possessing an approximately 1.3-kbp insert was retained for subsequent analyses. The sequence of the terminal ends of the selected clone reveals that the DNA sequence is the following: sequence of the pUC19 polylinker from the EcoRI to SacI sites, followed by the sequence of the oligonucleotides used in the cloning from which the 4 bp GATCC of the oligonucleotide 1 described above have been deleted, followed by the remainder of the sequence present in pRPA-ML-712 up to the HindIII site and sequence of the pUC19 polylinker from XbaI to HindIII. This clone was designated pRPA-ML-715.

7. Obtaining of a cDNA coding for a mutated maize EPSPS

All the mutagenesis steps were carried out with the Pharmacia U.S.E. mutagenesis kit according to the supplier's instructions. The principle of this mutagenesis system is as follows: plasmid DNA is denatured by heat and reassociated in the presence of a molar excess of, on the one hand the mutagenesis oligonucleotide, and on the other hand an oligonucleotide enabling a unique restriction enzyme site present in the polylinker to be eliminated. After the reassociation step, synthesis of the complementary strand is carried out by the action of T4 DNA polymerase in the presence of T4 DNA ligase and gene 32 protein in a suitable buffer which is supplied. The synthesis product is incubated in the presence of the restriction enzyme for which the site is assumed to have disappeared by mutagenesis. The E. coli strain possessing, in particular, the mutS mutation is used as host for the transformation of this DNA. After growth in liquid medium, the total plasmid DNA is prepared and incubated in the presence of the restriction enzyme used before. After these treatments, E. coli strain DH10B is used as host for the transformation. The plasmid DNA of the clones isolated is prepared, and the presence of the mutation introduced is verified by sequencing.

A)—modification of sites or sequences without in principle affecting the EPSPS-resistance character of maize to products which are competitive inhibitors of EPSP synthase activity: elimination of an internal NcoI site from pRPA-ML-715.

The pRPA-ML-715 sequence is numbered arbitrarily by placing the first base of the N-terminal alanine codon GCC at position 1. This sequence possesses an NcoI site at position 1217. The site-modification oligonucleotide possesses the sequence:

5'-CCACAGGATGGCGATGGCCTTCTCC-3'. (SEQ ID NO:11)

After sequencing according to the references given above, the sequence read after mutagenesis corresponds to that of the oligonucleotide used. The NcoI site has indeed been eliminated, and the translation into amino acids in this region preserves the initial sequence present in pRPA-ML-715.

This clone was designated pRPA-ML-716.

The 1340-bp sequence of this clone is presented in SEQ ID No. 2 and SEQ ID No. 3.

B)—sequence modifications enabling the EPSPS-resistance character of maize to products which are competitive inhibitors of EPSP synthase activity to be increased.

The following oligonucleotides were used:

a) mutation Thr 102→Ile.

5'-GAATGCTGGAATCGCAATGCGGCCATTGACAGC-3'
(SEQ ID NO:12)

b) mutation Pro 106→Ser.

5'-GAATGCTGGAACTGCAATGCGGTCCTTGACAGC-3'
(SEQ ID NO;13)

c) mutations Gly 101→Ala and Thr 102→Ile.

5'-CTTGGGGAATGCTGCCATCGCAATGCGGCCATTG-3'
(SEQ ID NO:14)

d) mutations Thr 102→Ile and Pro 106→Ser.

5'-GGGGAATGCTGGAATCGCAATGCGGTCCTTGACAGC-3'
(SEQ ID NO:15)

After sequencing, the sequence read after mutagenesis on the three mutated fragments is identical to the parent pRPA-ML-716 DNA sequence, with the exception of the mutagenized region which corresponds to that of the mutagenesis oligonucleotides used. These clones were designated: pRPA-ML-717 for the mutation Thr 102→Ile, pRPA-ML-718 for the mutation Pro 106→Ser, pRPA-ML-719 for the mutations Gly 101→Ala and Thr 102→Ile and pRPA-ML-720 for the mutations Thr 102→Ile and Pro 106→Ser.

The 1340-bp sequence of pRPA-ML-720 is presented in SEQ ID No. 4 and SEQ ID No. 5.

The 1395-bp NcoI-HindIII insert is the basis of all the constructions used for the transformation of plants for the introduction of resistance to herbicides which are competitive inhibitors of EPSPS, and especially glyphosate resistance. This insert will be designated in the remainder of the description "the maize EPSPS double mutant".

EXAMPLE 2

Glyphosate Tolerance of the Different Mutants In Vitro 2.a: Extraction of EPSP synthase The different EPSP synthase genes are introduced in the form of an NcoI-HindIII cassette into the plasmid vector pTro99a (Pharmacia, ref: 27-5007-01) cut with NcoI and HindIII. Recombinant E. coli DH10B bacteria overexpressing the different EPSP synthases are sonicated in 40 ml of buffer per 10 g of pelleted cells, and washed with this same buffer (200 mM Tris-HCl pH 7.8, 50 mM mercaptoethanol, 5 mM EDTA and 1 mM PMSF), to which 1 g of polyvinylpyrrolidone is added. The suspension is stirred for 15 minutes at 4° C. and then centrifuged for 20 minutes at 27,000 g and 4° C.

Ammonium sulphate is added to the supernatant to bring the solution to 40% saturation with respect to ammonium sulphate. The mixture is centrifuged for 20 minutes at 27,000 g and 4° C. Ammonium sulphate is added to the new supernatant to bring the solution to 70% saturation with respect to ammonium sulphate. The mixture is centrifuged for 30 minutes at 27,000 g and 4° C. The EPSP synthase present in this protein pellet is taken up in 1 ml of buffer (20 mM Tris-HCl pH 7.8 and 50 mM mercaptoethanol). This solution is dialysed overnight against two liters of this same buffer at 4° C.

2.b: Enzyme activity

The activity of each enzyme, as well as its glyphosate resistance, is measured in vitro over 10 minutes at 37° C. in the following reaction mixture: 100 mM maleic acid pH 5.6, 1 mM phosphoenolpyruvate, 3 mM shikimate 3-phosphate (prepared according to Knowles P. R. and Sprinson D. B. 1970. Methods in Enzymol 17A, 351–352 from Aerobacter aerogenes strain ATCC 25597) and 10 mM potassium fluoride. The enzyme extract is added at the last moment after the addition of glyphosate, the final concentration of which varies from 0 to 20 mM.

The activity is measured by assaying the phosphate liberated according to the technique of Tausky H. A. and Shorr E. 1953. J. Biol. Chem. 202, 675–685.

Under these conditions, the wild-type (WT) enzyme is already 85% inhibited at a glyphosate concentration of 0.12 mM. At this concentration, the mutant enzyme known as Ser106 is only 50% inhibited, and the other three mutants, Ile102, Ile102/Ser106 and Ala101/Ile102, show little or no inhibition.

The glyphosate concentration has to be multiplied by ten, that is to say 1.2 mM, in order to produce a 50% inhibition of the mutant enzyme Ile102, the mutants Ile102/Ser106, Ala/Ile and Ala still not being inhibited.

It should be noted that the activity of the mutants Ala/Ile and Ala is not inhibited up to glyphosate concentrations of 10 mM, and that that of the mutant Ile102/Ser106 is not reduced even if the glyphosate concentration is multiplied by 2, that is to say 20 mM.

EXAMPLE 3

Resistance of Transformed Tobacco Plants 1-1—Transformation

The vector pRPA-RD-173 is introduced into Agrobacterium tumefaciens strain EHA101 (Hood et al., 1987) carrying the cosmid pTVK291 (Komari et al., 1986). The transformation technique is based on the procedure of Horsh et al. (1985).

1-2—Regeneration

The regeneration of PBD6 tobacco (source SEITA France) from leaf explants is carried out on a Murashige and Skoog (MS) basal medium comprising 30 g/l of sucrose as well as 200 µg/ml of kanamycin. The leaf explants are removed from plants cultivated in the greenhouse or in vitro and are transformed according to the leaf disc technique (Science, 1985, Vol. 227, pp. 1229–1231) in three successive steps: the first comprises the induction of shoots on a medium supplemented with 30 g/l of sucrose containing 0.05 mg/l of naphthylacetic acid (NAA) and 2 mg/l of benzylaminopurine (BAP) for 15 days. The shoots formed during this step are then developed for 10 days by culturing on an MS medium supplemented with 30 g/l of sucrose but not containing any hormone. Shoots which have developed are then removed and cultured on an MS rooting medium having half the content of salts, vitamins and sugar and not containing any hormone. After approximately 15 days, the rooted shoots are transferred to soil.

1-3—Glyphosate resistance

Twenty transformed plants were regenerated and transferred to the greenhouse for the construction of pRPA-RD-173. These plants were treated in the greenhouse at the 5-leaf stage with an aqueous suspension of RoundUp corresponding to 0.8 kg of glyphosate active substance per hectare.

The results correspond to the observation of phytotoxicity indices recorded 3 weeks after treatment. Under these conditions, it is found that the plants transformed with the construction pRPA-RD-173 display very good tolerance, whereas the untransformed control plants are completely destroyed.

These results show clearly the improvement brought about by the use of a chimeric gene according to the invention for the same gene coding for glyphosate tolerance.

EXAMPLE 4

Transformation and Selection of Maize Cells

BMS (Black Mexican Sweet) maize cells in an exponential growth phase are bombarded with the construction pRPA-RD-130 according to the principle and the protocol described by Klein et al. 1987 (Klein T. M., Wolf E. D., Wu R. and Sandford J. C. (1987): High velocity microprojectiles for delivering nucleic acids into living cells, NATURE Vol. 327 pp. 70–73).

Two days after bomardment, the cells are transferred to the same medium containing 2 mM N-(phosphonomethyl) glycine.

After 8 weeks of selection on this medium, calluses which develop are selected, then amplified and analysed by PCR, and reveal clearly the presence of the chimeric OPT-EPSPS gene.

Cells not bombarded and grown on the same medium containing 2 mM N-(phosphonomethyl)glycine are blocked by the herbicide and do not develop.

The transformed plants according to the invention may be used as parents for obtaining lines and hybrids having the phenotypic character corresponding to the expression of the chimeric gene introduced.

Description of the constructions of the plasmids pRPA-RD-124: Addition of a "nos" polyadenylation signal to pRPA-ML-720 with creation of a cloning cassette containing the maize double mutant EPSPS gene (Thr 102→Ile and Pro 106→Ser). pRPA-ML-720 is digested with HindIII and treated with the Klenow fragment of E. coli DNA polymerase I to produce a blunt end. A second digestion is performed with NcoI, and the EPSPS fragment is purified. The EPSPS gene is then ligated with purified pRPA-RD-12 (a cloning cassette containing the polyadenylation signal of nopaline synthase) to give pRPA-RD-124. To obtain the useful purified vector pRPA-RD-12, it was necessary for the latter to be digested beforehand with SalI, treated with Klenow DNA polymerase and then digested a second time with NcoI.

pRPA-RD-125: Addition of an optimized transit peptide (OTP) to pRPA-RD-124 with creation of a cloning cassette containing the EPSPS gene targeted on the plasmids. pRPA-RD-7 (European Patent Application EP 652 286) is digested with SphI, treated with T4 DNA polymerase and then digested with SpeI, and the OPT fragment is purified. This OTP fragment is cloned into pRPA-RD-124 which has previously been digested with NcoI, treated with Klenow DNA polymerase to remove the protruding 3' portion and then digested with SpeI. This clone is then sequenced in order to ensure correct translational fusion between OTP and the EPSPS gene. pRPA-RD-125 is then obtained.

pRPA-RD-130: Addition of the H3C4 maize histone promoter and of adh1 intron 1 sequences of pRPA-RD-123 (Patent Application EP 507 698) to pRPA-RD-125 with creation of a cassette for expression in plants for the expression of the double mutant EPSPS gene in the tissues of monocotyledons. pRPA-RD-123 (a cassette containing the H3C4 maize histone promoter fused with the adh1 intron 1) is digested with NcoI and SacI. The DNA fragment containing the promoter derived from pRPA-RD-123 is then purified and ligated with pRPA-RD-125 which has previously been digested with NcoI and SacI.

pRPA-RD-159: Addition of the H4A748 Arabidoposis histone double promoter (Patent Application EP 507 698) to pRPA-RD-125 with creation of a cassette for expression in plants for the expression of the "OTP-double mutant EPSPS gene" gene in the tissues of dicytyledons. pRPA-RD-132 (a cassette containing the H4A748 double promoter (Patent Application EP 507 698)) is digested with NcoI and SacI. The purified promoter fragment is then cloned into pRPA-RD-125 which has been digested with EcoI and SacI.

pRPA-RD-173: Addition of the "H4A748 promoter-OTP-double mutant EPSPS gene" gene of pRPA-RD-159 to plasmid pRPA-BL-150A (European Patent Application 508 909) with creation of an Agrobacterium tumefaciens transformation vector. pRPA-RD-159 is digested with NotI and treated with Klenow polymerase. This fragment is then cloned into pRPA-BL-150A with SmaI.

What is claimed is:

1. A modified plant DNA molecule encoding a modified EPSPS enzyme wherein said enzyme comprises:

a first amino substitution from threonine to isoleucine at the threonine which corresponds to position 102 of the amino acid sequence of SEQ ID NO: 3; and a second amino acid substitution from proline to serine at the proline which corresponds to position 106 of the amino acid sequence of SEQ ID NO: 3.

2. The modified plant DNA molecule as claimed in claim 1 wherein the modified plant DNA molecule is of maize origin.

3. An isolated polynucleotide molecule having the sequence of SEQ ID NO: 4.

4. A vector comprising the following components, which are operably associated in the direction of transcription:

(a) a promoter functional in a plant cell; and (b) the modified plant DNA molecule of claim 1.

5. The vector of claim 4 further comprising a nucleic acid encoding a chloroplast transit peptide operably associated with, and in the order of transcription between, the promoter functional in a plant cell and the modified plant DNA molecule.

6. A transformed plant cell comprising a vector comprising the following components, which are operably associated in the direction of transcription:

(a) a promoter functional in a plant cell;

(b) a nucleic acid encoding a chloroplast transit peptide;

(c) a modified DNA molecule of maize origin encoding a modified EPSPS enzyme wherein said enzyme comprises:

a first amino acid substitution from threonine to isoleucine at the threonine which corresponds to position 102 of the amino acid sequence of SEQ ID NO: 3; and a second amino acid substitution from proline to serine at the proline which corresponds to position 106 of the amino acid sequence of SEQ ID NO: 3; and (d) an untranslated transcription termination signal region.

7. The plant cell of claim 6 which is a monocot plant cell with increased tolerance to glyphosate herbicides relative to a non-transformed plant cell.

8. The plant cell of claim 6 which is a dicot plant cell with increased tolerance to glyphosate herbicide relative to a non-transformed plant cell.

9. A transgenic plant comprising a vector comprising the following components, which are operably associated in the direction of transcription:

(a) a promoter functional in a plant cell;

(b) a nucleic acid encoding a chloroplast transit peptide;

(c) a modified DNA molecule of maize origin encoding a modified EPSPS enzyme wherein said enzyme comprises:

a first amino acid substitution from threonine to isoleucine at the threonine which corresponds to position 102 of the amino acid sequence of SEQ ID NO: 3; and a second amino acid substitution from proline to serine at the proline which corresponds to position 106 of the amino acid sequence of SEQ ID NO: 3; and (d) an untranslated transcription termination signal region.

10. The transgenic plant of claim 9 which is a monocot with increased tolerance to glyphosate herbicides relative to a non-transgenic plant.

11. The transgenic plant of claim 9 which is a dicot with increased tolerance to glyphosate herbicides relative to a non-transgenic plant.

12. A method for selectively controlling plants which method comprises the steps of:

a) planting crop seeds or plants which have increased glyphosate tolerance as a result of a chimeric gene being inserted into said crop seeds or plants, said chimeric gene having (i) a promoter region functional in a plant cell; and (ii) a modified plant DNA molecule encoding a modified EPSAPS enzyme wherein said enzyme comprises:

a first amino acid substitution from threonine to isoleucine at the threonine which corresponds to position 102 of the amino acid sequence of SEQ ID NO: 3; and a second amino acid substitution from proline to serine at the proline which corresponds to position 106 of the amino acid sequence of SEQ ID NO: 3; and (iii) an untranslated transcription termination signal region; and b) applying to said crop seeds or plants a sufficient amount of glyphosate to control untransformed plants without significantly affecting said crop seeds or plants that comprise the chimeric gene.

13. A plant transformed with a modified DNA molecule encoding a plant EPSPS enzyme having a first amino acid substitution from threonine to isoleucine at the threonine which corresponds to position 102 of the amino acid sequence of SEQ ID NO: 3; and a second amino acid substitution from proline to serine at the proline which corresponds to position 106 of the amino acid sequence of SEQ ID NO: 3.

\* \* \* \* \*

(12) EX PARTE REEXAMINATION CERTIFICATE (6076th)
United States Patent
Lebrun et al.

(10) Number: US 6,566,587 C1
(45) Certificate Issued: Jan. 1, 2008

(54) MUTATED 5-ENOLPYRUVYLSHIKIMATE-3-PHOSPHATE SYNTHASE, GENE CODING FOR SAID PROTEIN AND TRANSFORMED PLANTS CONTAINING SAID GENE

(75) Inventors: Michel Lebrun, Lyons (FR); Alain Sailland, Lyons (FR); Georges Freyssinet, St Cyr Au Mont d'Or (FR); Eric Degryse, Strasbourg (FR)

(73) Assignee: Bayer CropScience S.A., Lyons (FR)

Reexamination Request:
No. 90/007,905, Jan. 31, 2006

Reexamination Certificate for:
Patent No.: 6,566,587
Issued: May 20, 2003
Appl. No.: 08/945,144
Filed: Jan. 20, 1998

(22) PCT Filed: Jul. 18, 1996
(86) PCT No.: PCT/FR96/01125
§ 371 (c)(1),
(2), (4) Date: Jan. 20, 1998
(87) PCT Pub. No.: WO97/04103
PCT Pub. Date: Feb. 6, 1997

(30) Foreign Application Priority Data
Jul. 19, 1995 (FR) .......................................... 95 08979

(51) Int. Cl.
*C12N 15/82* (2006.01)
*C12N 9/10* (2006.01)

(52) U.S. Cl. .................... 800/300; 435/320.1; 435/419; 536/23.6; 800/278; 800/287; 800/320.1; 47/58.1 R

(58) Field of Classification Search ........................ None
See application file for complete search history.

(56) References Cited

U.S. PATENT DOCUMENTS 4,769,061 A * 9/1988 Comai ........................ 504/206

FOREIGN PATENT DOCUMENTS

WO 95/06128 * 3/1995

OTHER PUBLICATIONS

S.R. Padgette et al., J. Biol. Chem. 266(33) pp. 22364–22369 (1991).*
D. M. Stalker et al. J. Biol. Chem. vol. 25, pp. 4724–4728 (1985).*
Stallings et al., Proc. Nat'l. Acad. Sci. USA 88 : pp. 5046–5050 (1991).*

* cited by examiner

*Primary Examiner*—Padmashri Ponnaluri

(57) ABSTRACT

The present invention relates to DNA molecules of plant origin encoding a modified 5-enolpyruvylshikimate-3-phosphate synthase (EPSPS) enzyme wherein the a first EPSPS coding sequence that normally encodes a threonine residue of a mature EPSPS sequence is modified to encode isoleucine of the mature EPSPS sequence, and a second EPSPS coding sequence that normally encodes a proline residue of a mature EPSPS sequence is modified to encode serine of the mature EPSPS sequence, wherein the first and second residues are respectively located at relatively positions 102 and 106 of a mature EPSPS sequence encoded by said DNA molecule; and the production of a transgenic plant resistance or tolerant to a herbicide of the phosphonomethylglycine family, e.g., glyphosate. The mutated enzyme, which substantially maintains the catayltic activity of the wild-type enzyme, allows for increased tolerance or tolerance of the plant to a herbicide of the phosphonomethylglycine family, and allows for the substantially normal growth or development of the plant, its organs, tissues or cells.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 3, 9, 10, 11 and 13 is confirmed.

Claim 2 is cancelled.

Claims 1, 4, 6 and 12 are determined to be patentable as amended.

Claims 5, 7 and 8, dependent on an amended claim, are determined to be patentable.

1. A modified plant DNA molecule encoding [a modified EPSPS enzyme wherein said enzyme comprises:
    a first amino substitution from threonine to isoleucine at the threonine which corresponds to position 102 of the amino acid sequence of SEQ ID NO: 3; and
    a second amino acid substitution from proline to serine at the proline which corresponds to position 106 of the amino acid sequence of] SEQ ID NO: [3] *5*.

4. A vector comprising the following components, which are operably associated in the direction of transcription:
    (a) a promoter functional in a plant cell; and
    (b) [the modified plant DNA molecule of claim 1] *a modified plant DNA molecule encoding SEQ ID NO: 5*.

6. A transformed plant cell comprising a vector comprising the following components, which are operably associated in the direction of transcription:
    (a) a promoter functional in a plant cell;
    (b) a nucleic acid encoding a chloroplast transit peptide;
    (c) a modified DNA molecule of maize origin encoding [a modified EPSPS enzyme wherein said enzyme comprises:
        a first amino acid substitution from threonine to isoleucine at the threonine which corresponds to position 102 of the amino acid sequence of SEQ ID NO: 3; and
        a second amino acid substitution from proline to serine at the proline which corresponds to position 106 of the amino acid sequence of] SEQ ID NO: [3] *5*; and
    (d) an untranslated transcription termination signal region.

12. A method for selectively controlling plants which method comprises the steps of:
    a) planting crop seeds or plants which have increased glyphosate tolerance as a result of a chimeric gene being inserted into said crop seeds or plants, said chimeric gene having
        (i) a promoter region functional in a plant cell; and
        (ii) a modified plant DNA molecule encoding a modified [EPSAPS] *EPSPS* enzyme wherein said enzyme comprises:
            a first amino acid substitution from threonine to isoleucine at the threonine which corresponds to position 102 of the amino acid sequence of SEQ ID NO: 3; and
            a second amino acid substitution from proline to serine at the proline which corresponds to position 106 of the amino acid sequence of SEQ ID NO: 3; and
        (iii) an untranslated transcription termination signal region; and
    b) applying to said crop seeds or plants a sufficient amount of glyphosate to control untransformed plants without significantly affecting said crop seeds or plants that comprise the chimeric gene.

* * * * *